United States Patent
Takemoto et al.

(10) Patent No.: US 10,674,978 B2
(45) Date of Patent: Jun. 9, 2020

(54) MOVING TYPE RADIATION DEVICE

(71) Applicant: Shimadzu Corporation, Kyoto (JP)

(72) Inventors: Hajime Takemoto, Kyoto (JP); Toru Hayakawa, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 25 days.

(21) Appl. No.: 16/081,284

(22) PCT Filed: Mar. 1, 2016

(86) PCT No.: PCT/JP2016/056296
§ 371 (c)(1),
(2) Date: Aug. 30, 2018

(87) PCT Pub. No.: WO2017/149672
PCT Pub. Date: Sep. 8, 2017

(65) Prior Publication Data
US 2019/0069860 A1    Mar. 7, 2019

(51) Int. Cl.
*H05G 1/02* (2006.01)
*A61B 6/00* (2006.01)

(52) U.S. Cl.
CPC ............ *A61B 6/447* (2013.01); *A61B 6/4405* (2013.01); *A61B 6/588* (2013.01); *H05G 1/02* (2013.01)

(58) Field of Classification Search
CPC ....... A61B 6/588; A61B 6/447; A61B 6/4405; H05G 1/02
See application file for complete search history.

(56) References Cited

U.S. PATENT DOCUMENTS 5,283,823 A  *  2/1994  Morris ................. A61B 6/4405
                                                    378/193
RE47,581 E  *  8/2019  Moreno Vallejo ... A61B 6/4405
(Continued)

FOREIGN PATENT DOCUMENTS

EP          2859849 A1    4/2015
JP         H08-200206 A   8/1996
(Continued)

OTHER PUBLICATIONS

International Search Report dated May 31, 2016 for PCT application PCT/JP2016/056296.
(Continued)

*Primary Examiner* — Kiho Kim
(74) *Attorney, Agent, or Firm* — Muir Patent Law, PLLC

(57) ABSTRACT

According to the present invention, a highly safe moving-type radiation device can be provided. In the case of a conventional configuration using tension springs, if a spring is severed, the fragments will separate from each other permanently. Therefore, the present invention uses compression spring 8a and 8b instead. According to the spring mechanism of the present invention, even if a shaft is about to move largely in accordance with the severing of a spring, fragments of the spring, which has become stuck each other and immovable, interfere and prevent the movement of the shaft. What has been devised in the present invention is a junction spring seat that links a plurality of compression springs 8a and 8b. With this, even in cases where the compression springs 8a and 8b are linked in series, the compression springs 8a and 8b will not be buckled.

12 Claims, 13 Drawing Sheets

(56) References Cited

U.S. PATENT DOCUMENTS

| | | |
|---|---|---|
| 2003/0178758 A1 | 9/2003 | Metelski et al. |
| 2005/0179878 A1* | 8/2005 | Ohtsuka ............... A61B 6/4216 355/30 |
| 2005/0281388 A1 | 12/2005 | Boomgaarden et al. |
| 2010/0091942 A1* | 4/2010 | Pohjoispuro ............. A61B 6/14 378/38 |
| 2011/0249804 A1 | 10/2011 | Wendlandt et al. |
| 2011/0249805 A1* | 10/2011 | Kralles ................ A61B 6/4405 378/198 |
| 2011/0249806 A1 | 10/2011 | Wendlandt et al. |
| 2011/0249807 A1 | 10/2011 | Dirisio et al. |
| 2012/0224673 A1* | 9/2012 | Barker ................ A61B 6/4405 378/198 |
| 2014/0098942 A1* | 4/2014 | Omura ................ A61B 6/4405 378/197 |
| 2014/0098943 A1* | 4/2014 | Omura ................ A61B 6/4452 378/198 |
| 2014/0133627 A1* | 5/2014 | Sakuragi ............. A61B 6/4429 378/62 |
| 2016/0015342 A1* | 1/2016 | Okuno ................... A61B 6/447 378/62 |
| 2016/0199013 A1 | 7/2016 | Moreno Vallejo et al. |
| 2017/0303882 A1* | 10/2017 | Ficarra .................... A61B 6/102 |
| 2018/0242933 A1* | 8/2018 | Sanbuichi ................ A61B 6/00 |
| 2019/0357863 A1* | 11/2019 | Dirisio ................ A61B 6/4405 |

FOREIGN PATENT DOCUMENTS

| | | |
|---|---|---|
| JP | H10-288234 A | 10/1998 |
| JP | 2002-155979 A | 5/2002 |
| JP | 2003-301879 A | 10/2003 |
| JP | 2004-033415 A | 2/2004 |
| JP | 2005-349197 A | 12/2005 |
| JP | 2009-174431 A | 8/2009 |
| JP | 2011-163380 A | 8/2011 |
| JP | 2013-523397 A | 6/2013 |
| JP | 2013-523398 A | 6/2013 |
| JP | 2013-523400 A | 6/2013 |

OTHER PUBLICATIONS

Written Opinion of the International Searching Authority dated May 31, 2016 for PCT application PCT/JP2016/056296.

* cited by examiner

MOVING TYPE RADIATION DEVICE

TECHNICAL FIELD

The present invention relates to a moving-type radiation device used for the rounds for patients, and more particularly to a moving-type radiation imaging device equipped with a mechanism for adjusting height of a radiation source.

BACKGROUND ART

FIG. 13 illustrates a moving-type radiation device of a conventional configuration. In this device, a radiation source 56 for irradiating radiation and a support column 52 supporting the radiation source 56 and extending in a vertical direction are provided on a hand-truck carriage. The support column 52 slidably supports the radiation source 56. The radiation source 56 is configured to be moved in the vertical direction while being supported by the support column 52. Such a device has electric assist, and is devised so that the operator can move easily without applying a strong force by hands.

Such a moving-type radiation device can be moved to a subject's room. By using this device, it becomes possible to perform radiation imaging of the subject without moving the subject as much as possible.

FIG. 14 schematically illustrates a mechanism for realizing the movements of the radiation source 56 in the vertical direction. The left side of FIG. 14 illustrates a typical mechanism of this device which uses a counter weight W having the same weight as the radiation source 56. That is, the device on the left side of FIG. 14 is provided with a wire having one end connected to the radiation source 56 and the other end connected to the counter weight W, and the wire is held by the pulley. In this way, the radiation source 56 and the counter weight W are related by a well bucket type mechanism. The load applied to one end side of the wire is equal to the load applied to the other end side thereof. Therefore, the radiation source 56 and the counter weight W are balanced with each other, and therefore they do not move by themselves. Then, when a force is applied to the radiation source 56, the radiation source 56 easily moves up and down.

The radiation source 56 has a considerable weight. The mechanism on the left side of FIG. 14 requires a counter weight W of the same weight as the radiation source 56. Therefore, when the radiation source 56 is installed on the device, the device increases in weight by the weight of the radiation source 56. Therefore, the moving-type radiation imaging device adopting this mechanism becomes considerably heavy. When the moving-type radiation imaging device is heavy, it is difficult to move it.

Therefore, a mechanism capable of reducing the weight of the moving-type radiation imaging device has been proposed (see Patent Document 1). The right side of FIG. 14 illustrates this new mechanism. This mechanism has a configuration in which the counter weight W on the left side of FIG. 14 is replaced with a tension spring. By removing the counter weight W, the weight of the device can be reduced by an amount equivalent to the weight of the radiation source 56.

In the mechanism shown on the right side of FIG. 14, the force transmitted by the radiation source 56 to the pulley is balanced with the tensile force of the tension spring. Therefore, the radiation source 56 and the tensile force of the spring are balanced with each other and radiation source 56 does not move by itself. Then, when a force is applied to the radiation source 56, the radiation source 56 easily moves up and down.

The tension spring has a property that the tensile force changes when the elongation of the spring changes. Therefore, in order to constantly balance the load of the radiation source 56 and the tensile force of the spring, some ingenuity is required. The pulley on the right side of FIG. 14 is a combination of a spiral winding drum and a cylindrical winding drum. In this case, the spiral winding drum denotes a fixed pulley having a round shaft whose radius changes according to the rotation angle. As the spiral, specifically, a spiral of Archimedes can be exemplified, but it is not always necessary to use a spiral of Archimedes. As the tension spring stretches, the tensile force increases, but the radius of the spiral decreases by that amount. To the contrary, when the tension spring contracts and the tensile force weakens, the radius of the spiral increases by that amount. As a result, the same torque is always applied to the pulley. Therefore, the radiation source 56 is moved up and down in the same behavior as when the counter weight W is used.

PRIOR ART

Patent Document

Patent Document 1: Japanese Unexamined Patent Application Publication No. 2004-033415

SUMMARY OF THE INVENTION

Problems to be Solved by the Invention

However, the moving-type radiation device of the conventional configuration has the following problems.

That is, the moving-type radiation device of the conventional configuration is inadequate in terms of safety.

The tension spring described on the right side of FIG. 14 has a possibility of being severed due to aged deterioration, etc. It is not easy to prevent this severing of the spring. The left side of FIG. 15 shows a state in which the tension spring is severed. As the aged deterioration progresses, the tension spring may be severed suddenly, resulting in a state in which the front and back portions are divided as shown on the right side of FIG. 15. As a result, the power to control the falling of the radiation source 56 disappears, and therefore the radiation source 56 slides down vertically downward.

Because of this situation, the conventional configuration has been devised so that safety can be secured even if the radiation source 56 which is a load object falls. That is, in the conventional configuration, a safety mechanism for preventing falling of the radiation source 56 is provided separately. Therefore, even if the tension spring is severed, it is practically prevented that the radiation source 56 falls as it is and leads to an accident.

However, a safety mechanism is not always fully operational. It is also difficult to completely eliminate the time from the severing of the tension spring to the operation of the safety device. Even if a safety mechanism is equipped, if the tension spring is severed, the radiation source 56 will fall to a certain extent. Such circumstances are undesirable from the viewpoint of safety of the device.

The present invention has been made in view of the above-described circumstances, and its object is to provide a highly safe moving-type radiation device.

Means for Solving the Problems

The present invention has the following configuration to solve the above-mentioned problems.

That is, the moving-type radiation device according to the present invention includes:

a radiation source configured to irradiate radiation;

a support column configured to support the radiation source in an upwardly and downwardly movable manner and extending in a vertical direction;

an intermediate member provided at a position between the radiation source and the support column so as to be upwardly and downwardly movable in accordance with upward and downward movements of the radiation source;

a support column inner wire having one end connected to the intermediate member and the other end connected to an inside of the support column;

a support column inner pulley configured to support the support column inner wire and serve as a fixed pulley for the support column provided in the support column;

a relay pulley provided on the other end side of the support column inner wire when viewed from the support column inner pulley and configured to support the support column inner wire and serve as a fixed pulley for the support column provided in the support column;

a spring mechanism configured to give a tensile force to the support column inner wire and provided in the support column, wherein the spring mechanism includes:

(A) a plurality of compression springs arranged in series in a vertical direction;

(B1) a junction spring seat configured to connect the compression springs; and (C1) a vertically extended shaft provided so as to pass through an inside of the plurality of compression springs, the shaft being connected to one end of a spring unit configured by connecting the compression springs and configured to support the junction spring seat in an upwardly and downwardly movable manner.

[Functions and Effects] According to the present invention, it is possible to provide a highly safe moving-type radiation device. In the case of a conventional configuration using a tension spring, when a spring is severed, the fragments will separate from each other permanently. This becomes a cause of falling of the radiation source. Therefore, the present invention uses a compression spring instead of a tension spring. According to the spring mechanism of the present invention, even if the compression spring is severed, the fragments of the compression spring can only move from the tip seat to the junction spring seat. Such a situation is the same for the compression spring, even if it is severed, the fragments can only move from the end seat to the junction spring seat. This is because even if a shaft is about to move largely in accordance with the severing of the spring, fragments of the spring, which has become stuck each other and immovable, interfere and prevent the movement of the shaft. With this principle, the radiation source will not fall even if the spring is severed.

However, there is a characteristic feature that as the compression spring gets longer, it tends to become more bedable. The compression spring is difficult to secure a stroke. So, what has been devised in the present invention is a junction spring seat that links a plurality of compression springs. With this, even in cases where the compression springs are linked in series, the compression springs will not be buckled. That is, the junction spring seat is configured to be guided by the shaft, and does not escape in the lateral direction orthogonal to the extension direction of the spring. The individual compression springs are short enough and they will not be buckled.

Further, the moving-type radiation device according to the present invention includes:

a radiation source configured to irradiate radiation;

a support column configured to support the radiation source in an upwardly and downwardly movable manner and extending in a vertical direction;

an intermediate member provided at a position between the radiation source and the support column so as to be upwardly and downwardly movable in accordance with upward and downward movements of the radiation source;

a support column inner wire having one end connected to the intermediate member and the other end connected to an inside of the support column;

a support column inner pulley configured to support the support column inner wire and serve as a fixed pulley for the support column provided in the support column;

a relay pulley provided on the other end side of the support column inner wire when viewed from the support column inner pulley and configured to support the support column inner wire and serve as a fixed pulley for the support column provided in the support column; and a spring mechanism configured to give a tensile force to the support column inner wire and provided in the support column, wherein the spring mechanism includes:

(A) a compression spring arranged in a vertical direction;

(B2) an intermediate connector fixed in a middle of the compression spring; and (C2) a vertically extended shaft provided so as to pass through an inside of the compression spring, the shaft being connected to one end of the compression spring and configured to support the intermediate connector in an upwardly and downwardly movable manner.

[Functions and Effects] The present invention has a configuration which can exert the same effects described above with o single compression spring. The intermediate connector is configured to be guided by the shaft, and does not escape in the lateral direction orthogonal to the extending direction of the spring. Each part of the compression spring divided by the intermediate connector is sufficiently short and it will not be buckled.

Further, in the above-described moving-type radiation device, it is preferable to further include a tip spring seat connected to a spring closer to the support column inner pulley among the springs constituting the spring mechanism and configured to guide the shaft.

[Functions and Effects] According to the above-described configuration, it is possible to provide a configuration in which the shaft is assuredly guided by the tip spring seat.

Further, in the above-described moving-type radiation device, it is preferable that the tip spring seat be provided with a self-aligning mechanism.

[Functions and Effects] According to the above-described configuration, the tip spring seat can guide the inclined shaft smoothly.

Further, in the above-described moving-type radiation imaging device, it is more preferable to further include an intermediate member wire having one end connected to the radiation source and the other end connected to the support column or a base on which the support column is installed and an intermediate member pulley configured to support the intermediate member wire and serve as a fixed pulley for the intermediate member.

[Functions and Effects] The present invention is an example more concretely showing the movement of the intermediate member. The present invention can be carried out by incorporating it into the mechanism of the conventional configuration.

Further, in the above-described moving-type radiation device, it is more preferable that the intermediate member wire be multiplexed.

[Functions and Effects] The above-described configuration represents a more desirable configuration of the present invention. When the intermediate member wire is multiplexed, a more safe moving-type radiation device can be provided.

In the above-described moving-type radiation device, it is more preferable that the support column inner wire be multiplexed.

[Functions and Effects] The above-described configuration represents a more desirable configuration of the present invention. When the support column inner wire is multiplexed, a more safe moving-type radiation device can be provided.

In the above-described moving-type radiation device, it is more preferable to further include a sensor configured to sense severing of the support column inner wire.

[Functions and Effects] The above-described configuration represents a more desirable configuration of the present invention. When a sensor for sensing the severing of the support column inner wire, a more safe moving-type radiation device can be provided.

Effects of the Invention

According to the present invention, it is possible to provide a highly safe moving-type radiation device. In the case of a conventional configuration using a tension spring, if the spring is severed, the fragments will separate from each other permanently. Therefore, the present invention uses a compression spring instead. According to the spring mechanism of the present invention, even if a shaft is about to move largely in accordance with severing of a spring, fragments of the spring, which has become stuck each other and immovable, interfere and prevent the movement of the shaft. So, what has been devised in the present invention is a junction spring seat that links a plurality of compression springs. With this, even in cases where the compression springs are linked in series, the compression springs will not be buckled.

EMBODIMENTS FOR CARRYING OUT THE INVENTION

Next, the moving-type radiation device according to the present invention will be described. The device according to the present invention is a radiation device capable of moving to a patient's room by traveling a corridor of a hospital. By combining this device and a radiation detector, it is possible to capture a radiographic image of a subject even in a patient's room. The X-ray corresponds to the "radiation" of the present invention.

Example 1

Figure 1:
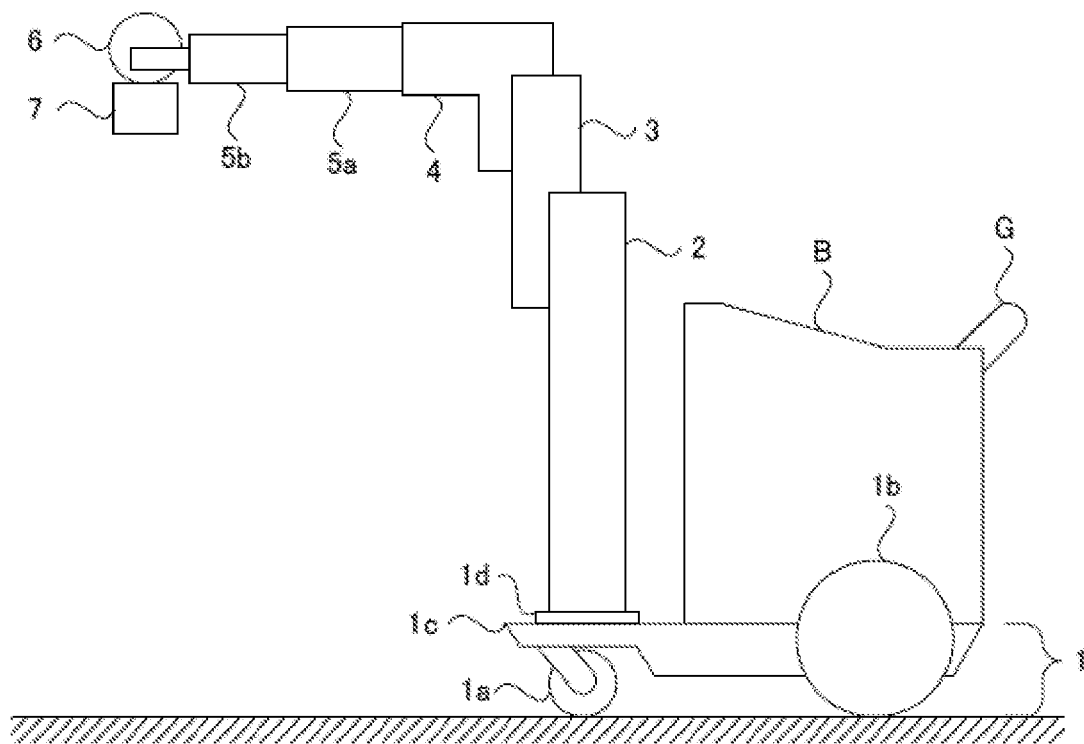
FIG. 1 is a plan view explaining an overall configuration of a moving-type X-ray device according to Example 1.

FIG. 1 shows an overall configuration of a moving-type X-ray device according to the present invention. The device according to the present invention is provided with a chassis 1 at the base portion of the device. The chassis 1 has a base 1*c* provided with two front wheels 1*a* and two rear wheels 1*b*. The chassis 1 is mounting other parts constituting the device. The chassis 1 is configured to support a support column 2.

A main body B is mounted on the chassis 1. The main body B is provided with a power supply device, a battery, an operation panel, a holder for housing a radiation detector, and the like. The main body B is provided with a grip G which an operator grasps when driving the device. It is configured such that when an operator applies a force to the grip G, an assist function provided in the chassis 1 works to assist the force given by the operator. With this, the operator can lightly move the device.

The support column 2 is a member extending in the vertical direction, and the inside is hollow. This support column 2 is rotatable about the axis extending in the vertical direction. This support column 2 can be rotated manually. This support column 2 supports the X-ray tube 6 described later in an upwardly and downwardly movable manner and extends in the vertical direction, and the inside is hollow.

The intermediate member 3 is a vertically elongated member provided so as to extend the support column 2. The support column 2 supports the intermediate member 3 in an upwardly and downwardly movable manner. The support column 2 is provided with a groove extending in the vertical direction configured to receive the intermediate member 3, and the intermediate member 3 can move in the vertical direction along this groove. The intermediate member 3 is provided at a position between the X-ray tube 6 and the support column 2 and moves upward and downward in accordance with the upward and downward movements of the X-ray tube 6.

The tip support column 4 is an L-shaped member provided so as to further extend the intermediate member 3. The intermediate member 3 supports the tip support column 4 so as to move upward and downward. The tip support column 4 has two arms orthogonal to each other, one arm extending in the vertical direction and the other arm extending in the horizontal direction. The intermediate member 3 is provided with a groove extending in the vertical direction configured to receive the vertical direction arm possessed by the tip support column 4, and the tip support column 4 can move in the vertical direction along this groove.

Figure 2:
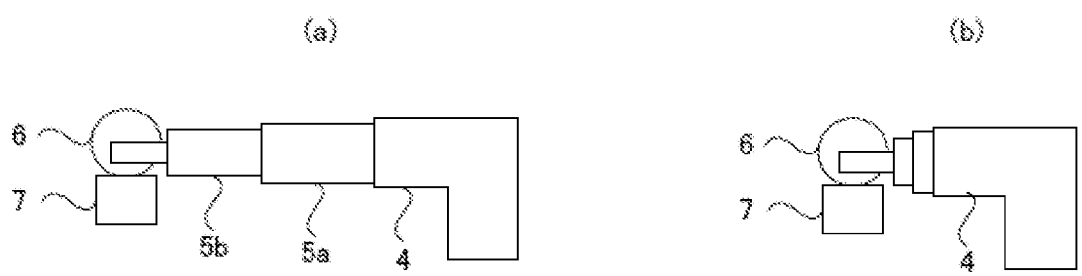
FIG. 2 is a schematic diagram explaining a lateral movement of an X-ray tube according to Example 1.

Lateral support columns 5a and 5b are horizontally elongated members extending in the horizontal direction. A horizontal arm possessed by the tip support column 4, the lateral support column 5a, and the lateral support column 5b are telescopically expandable and contractible. The left side of FIG. 2 shows the state in which the expansion structure is fully extended. The right side of FIG. 2 shows the state in which the expansion structure is fully contracted. This expansion/contraction mechanism can be manually operated.

The X-ray tube 6 is a device for generating X-rays. The X-ray tube 6 is a load object and has a considerable weight. The X-ray tube 6 is supported by a lateral support column 5b, and the support column 2, the intermediate member 3, the tip support column 4, and the lateral support columns 5a and 5b are configured to convey the load of the X-ray tube 6 to the chassis 1. The circuit related to the control of the X-ray tube 6 is housed in the main body B. Further, the X-ray tube 6 is provided with a collimator 7 for restricting the spread of X-rays. This collimator 7 moves following the movements of the X-ray tube 6. The X-ray tube 6 irradiates X-rays.

Figure 3:
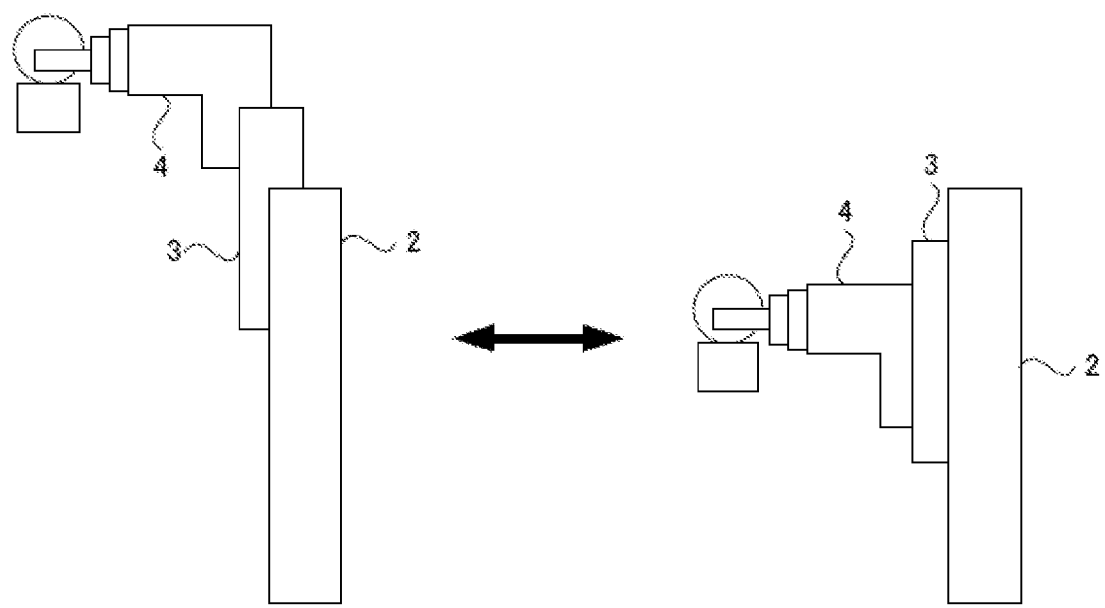
FIG. 3 is a schematic diagram explaining a vertical movement of an X-ray tube according to Example 1.

FIG. 3 illustrates the upward and downward movements of the tip support column 4. The left side of FIG. 3 illustrates the state in which the tip support column 4 is moved to the upper most position, and the right side of FIG. 3 illustrates the state in which the tip support column 4 is moved to the lower most position. When the tip support column 4 is moved in the vertical direction, the intermediate member 3 moves in conjunction with this. That is, it is configured such that when the tip support column 4 is moved in one direction by a certain movement amount, the intermediate member 3 is moved in the same direction by half of the movement amount.

As described above, according to the device of the present invention, it is configured such that the vertical movements of the X-ray tube 6 are served by the mechanism composed of the support column 2, the intermediate member 3 and the tip support column 4 and that the lateral movements of the X-ray tube 6 are served by the mechanism composed of the tip support column 4, the lateral support column 5a, and the lateral support column 5b. The rotational movements of the X-ray tube 6 are served by the support column 2. When a force that rotates the X-ray tube 6 about the vertical axis is applied, the support column 2 rotates with respect to the chassis 1. Then, the intermediate member 3, the tip support column 4, the lateral support columns 5a and 5b, and the X-ray tube 6 rotate so as to follow the support column 2 while keeping the positional relationship with the support column 2.

Figure 4:
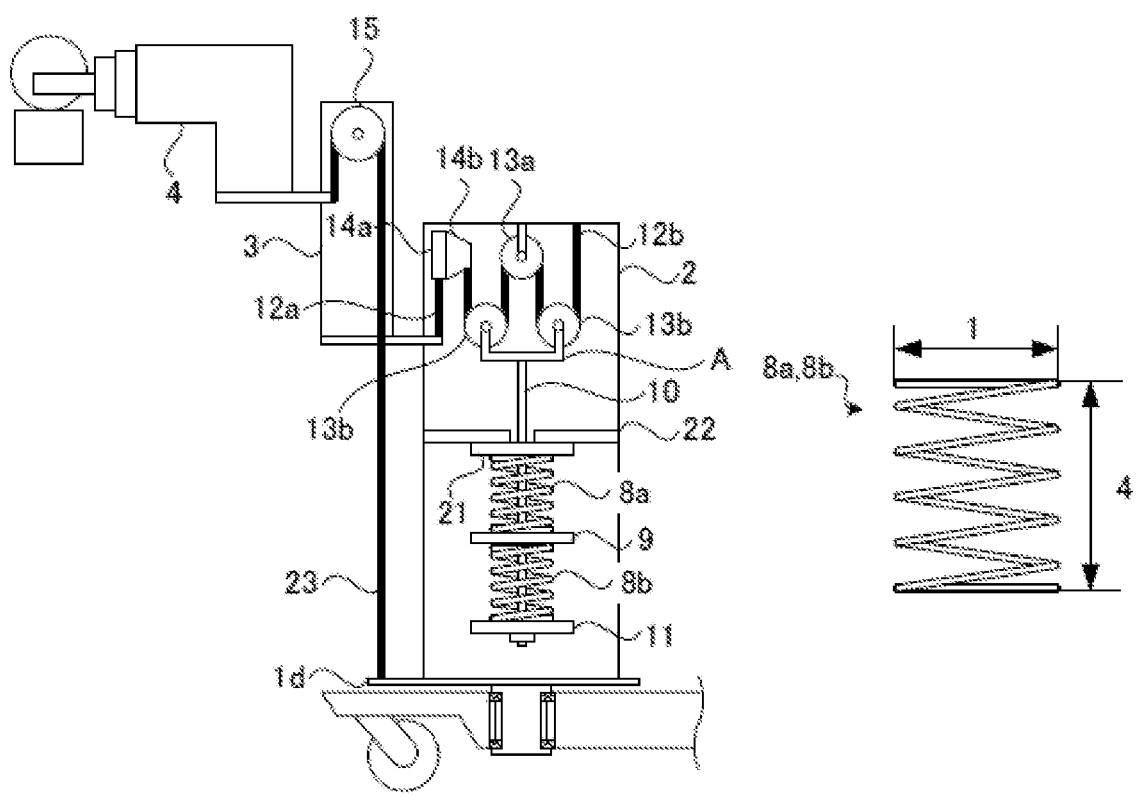
FIG. 4 is a cross-sectional view explaining a mechanism related to the vertical movement of the X-ray tube according to Example 1.

In the present invention, the characteristic feature is a mechanism which realizes the vertical movements of the X-ray tube 6. FIG. 4 explains this mechanism. To the tip support column 4 and the rotary base 1d mounted on the chassis, a fixing tool for fixing the tip of a wire is provided. Between these two fixing tools, an intermediate member wire 23 is provided. That is, one end of the intermediate member wire 23 is fixed to the fixing tool of the tip support column 4, and the other end thereof is fixed to the fixing tool of the rotary base 1d. The intermediate member wire 23 is retained in a state of being wrapped around the intermediate member pulley 15 provided in the intermediate member 3 so as to be in contact with the upper side of the intermediate member pulley 15. The intermediate member pulley 15 is a fixed pulley for the intermediate member 3.

The mechanism related to the intermediate member wire 23 will be briefly described. It is assumed that the intermediate member 3 in the state of FIG. 4 moves upward. In this case, looking at the movement of the intermediate member wire 23 with reference to the intermediate member pulley 15, the intermediate member wire 23 is wound up on the rotary base 1d side. Then, the intermediate member wire 23 between the intermediate member pulley 15 and the tip support column 4 becomes shorter, and the tip support column 4 rises accordingly. Further, it is assumed that the intermediate member 3 in the state of FIG. 4 moves downward. In this case, looking at the movement of the intermediate member wire 23 with reference to the intermediate member pulley 15, the intermediate member wire 23 is wound up on the tip support column 4 side. Then, the intermediate member wire 23 between the intermediate member pulley 15 and the tip support column 4 becomes longer, and the tip support column 4 descends accordingly. When the intermediate member 3 moves by a certain length, the intermediate member wire 23 is wound up twice the length, so the moving distance of the tip support column 4 becomes also twice the moving distance of the intermediate member 3.

The support column 2 is hollow, and is provided with various mechanisms in the inner hollow space of the support column 2. On the inner surface corresponding to the ceiling of the internal space of the support column, there is provided a fixing tool for fixing the tip of a wire. Similarly, the intermediate member 3 is also provided with a fixing tool.

In the support column, a winding pulley 14a and a spiral pulley 14b are provided. These pulleys 14a and 14b are fixed pulleys for the support column 2 and share the rotation shaft. The winding pulley 14a has a cylindrical shape, and is provided with a coiled groove. On the other hand, the spiral pulley 14b is a pulley having a wheel shaft whose radius ratio is variable, and has a tapered shape. The winding pulley 14a and the spiral pulley 14b are each provided with a fixing tool for fixing a tip of a wire.

In the winding pulley wire 12a, one end thereof is fixed to the fixing tool of the intermediate member 3 and the other end thereof is fixed to the fixing tool of the winding pulley 14a. The winding pulley wire 12a is held in the form wrapped around the winding pulley 14a. Therefore, the winding pulley wire 12a extends from the winding pulley wire 12a as a starting point and is held so as to unwind to the lower side of the winding pulley wire 12a.

The support column inner wire 12b has one end fixed to the fixing tool of the spiral pulley 14b and the other end fixed to the fixing tool provided in the support column 2. The support column inner wire 12b is held in the form wound around the spiral pulley 14b. Therefore, the support column inner wire 12b extends from the spiral pulley 14b as a starting point and is held so as to unwind toward the lower side of the spiral pulley 14b.

Inside the support column 2, between the support column inner pulley 14 and the fixing tool provided on the inner surface of the support column 2, a relay pulley 13a which is a fixed pulley for the support column 2 is provided. The relay pulley 13a supports the support column inner wire 12b. The support column inner wire 12b is held in a state of being wound on the relay pulley 13a so as to be in contact with the upper side of the relay pulley 13a. The relay pulley 13a is provided on the other end side of the support column inner wire 12b when viewed from the support column inner pulley 14 and is configured to support the support column inner wire 12b and serves as a fixed pulley for the support column 2 provided in the support column 2.

On each side of the relay pulley 13a, a movable pulley 13b is provided which moves with respect to the relay pulley 13a. The support column inner wire 12b is held in a state of being wound on the two movable pulleys 13b so as to be in contact with the lower side of the movable pulley 13b.

Therefore, starting from the fixing tool of the intermediate member 3, the support column inner wire 12b is wound on the support column inner pulley 14, the movable pulley 13b, the relay pulley 13a, and the movable pulley 13b one after another, and extends to the end point of the fixing tool provided on the inner surface of the support column 2.

<Arrangement Example of Mechanism>

Figure 5:
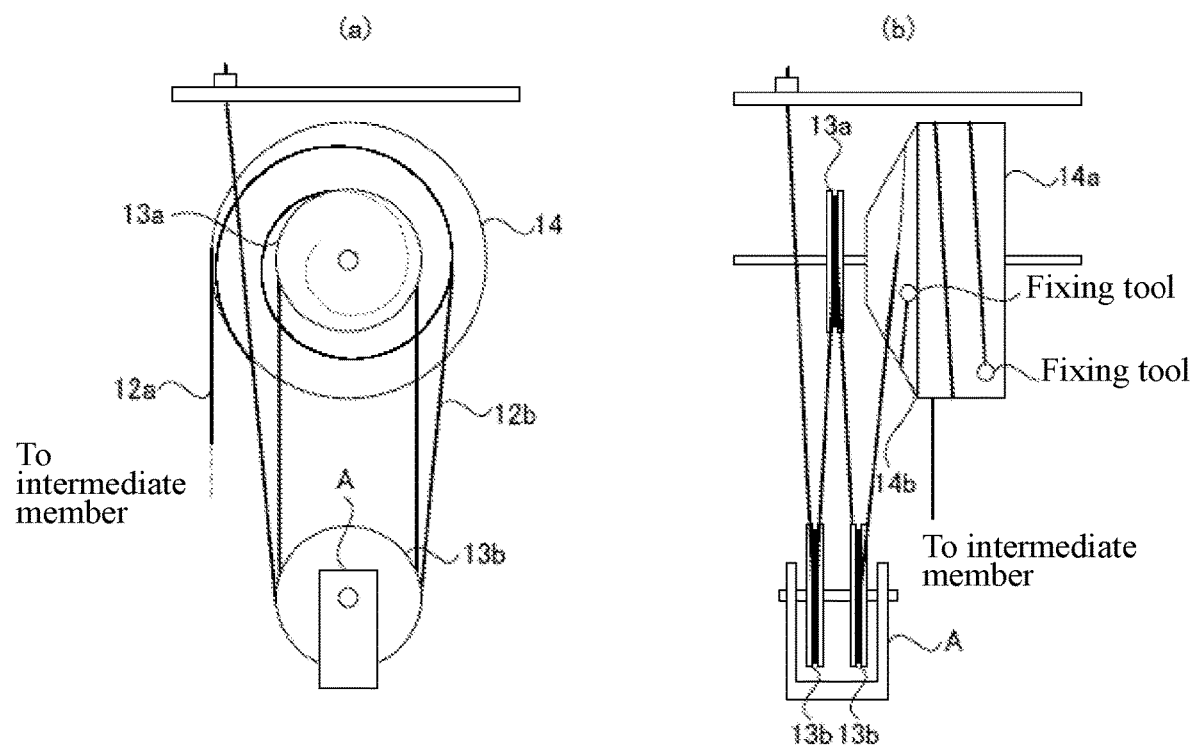
FIG. 5 is a schematic diagram showing a specific example of a mechanism according to Example 1.

The inside of the support column 2 shown in FIG. 4 is illustrated so that the transmission of power can be easy to understand. If the internal mechanism of the support column 2 is configured as shown in FIG. 4, the diameter of the support column 2 has to be made considerably large. On the other hand, FIG. 5 shows an arrangement example in which the same mechanism as in FIG. 4 is arranged in a more compact manner. According to such an arrangement example, it is possible to reduce the diameter of the support column 2.

The left side of FIG. 5 shows the arrangement example as viewed from the rotation axis direction of the support column inner pulley 14. According to the explanation with reference to FIG. 4, the rotation axis of the support column inner pulley 14 is depicted so as to be orthogonal to the rotation axis of the relay pulley 13a, but the rotation axes of the support column inner pulley 14 and the relay pulley 13a may be made to coincide with each other as shown on the left side of FIG. 5. Further, according to the explanation with reference to FIG. 4, the movable pulley 13b is arranged in a direction orthogonal to the rotation axis, but both the rotation axes may be arranged so as to coincide with each other as shown on the left side of FIG. 5. The right side of FIG. 5 shows the arrangement example as viewed from the direction orthogonal to the rotation axis of the support column inner pulley 14.

<Spring Mechanism>

Next, the spring mechanism which is a characteristic part of the present invention will be described. The spring mechanism generates a force to unwind the support column inner wire 12b from the support column inner pulley 14 by pulling the support column inner wire 12b downward via the two movable pulleys 13b. This force detains the downward movement of the intermediate member 3. The spring mechanism is a configuration that gives a tensile force to the support column inner wire 12b, and is provided in the support column 2.

The spring mechanism is provided with two coiled compression springs 8a and 8b arranged in series in the vertical direction. As shown on the right side of FIG. 4, in the compression springs 8a and 8b, it is preferable that the ratio of the diameter to the length be about 1:4 or less. This is because if the compression spring 8a, 8b is longer than this, buckling is likely to occur. The compression spring is a spring which, unlike the tension spring, gives a repulsive force when compressed to a certain object. As a familiar compression spring, there is a spring for holding a negative electrode provided in a dry battery holder. The spring mechanism links a plurality of compression springs 8a and 8b arranged in series in the vertical direction, and the junction spring seat 9 links the compression springs.

Figure 6:
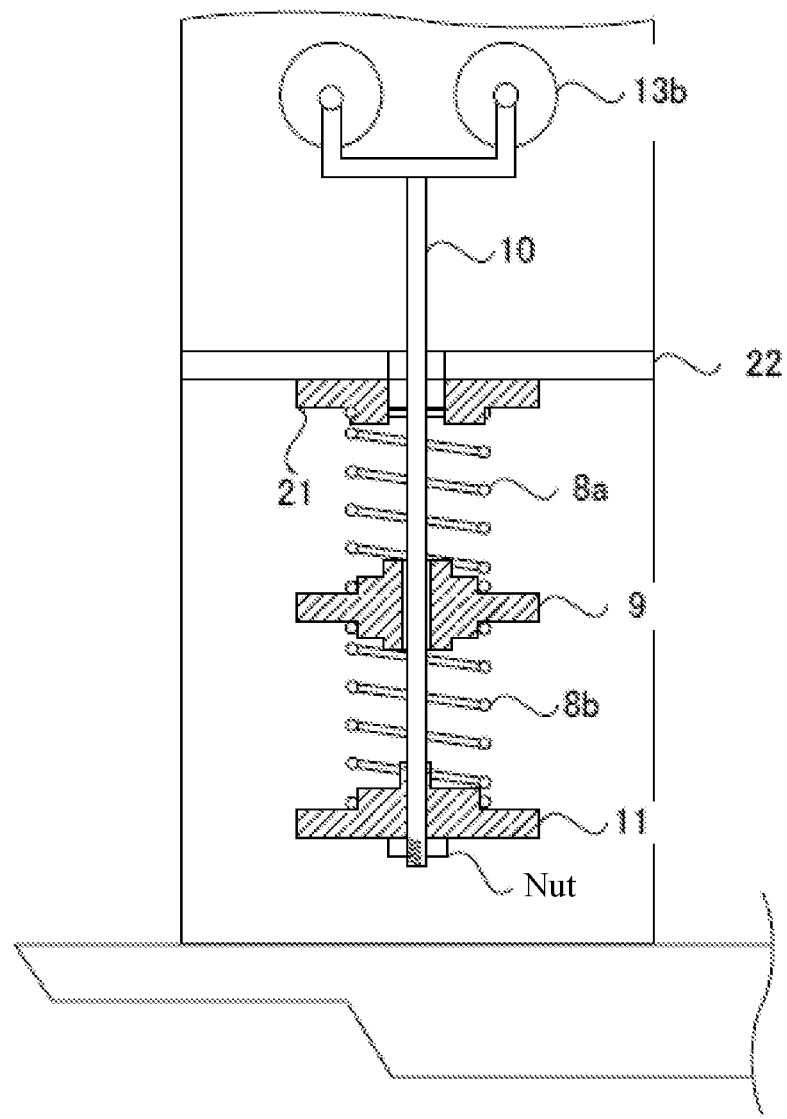
FIG. 6 is a cross-sectional view explaining a spring mechanism according to Example 1.

The two compression springs 8a and 8b are provided so as to be in contact with each other in the vertical direction with the same central axis. A disk-shaped junction spring seat 9 is provided at a position between the two compression springs 8a and 8b. The structure of this junction spring seat 9 will be described. FIG. 6 is a conceptual diagram for more easily explaining the structure of the spring mechanism. In FIG. 6, the cross-section of the compression spring 8a and its peripheral components is shown so that the inside of the compression spring 8a can be easily understood. To the junction spring seat 9, the end portions of different compression springs 8a and 8b are fitted from the upper and lower sides. The junction spring seat 9 is provided with cylindrically-shaped projections for fitting compression springs 8a and 8b on the upper and lower sides, the lower end of the compression spring 8a positioned at the lower side of both end of the compression spring 8a and the upper end of the compression spring 8b positioned at the upper end thereof fit in the corresponding projections, respectively. As a result, the compression springs 8a and 8b are connected to the junction spring seat 9. Further, the junction spring seat 9 is provided with a through-hole extending in the vertical direction. Inside the through-hole, a shaft 10, which will be described later, is disposed.

The compression springs 8a and 8b and the junction spring seat 9 linking them function like a single compression spring. So, the compression springs 8a and 8b and the junction spring seat 9 will be referred to as a spring unit. At the lower portion of the spring unit, a disc-shaped end spring seat 11 is provided. In the end spring seat 11, a cylindrically-shaped projection for fitting the compression spring 8b is provided at the top, and the lower end of both ends of the spring unit is connected to the end spring seat 11 by being fitted on this projection. Further, the end spring seat 11 is provided with a through-hole extending in the vertical direction. Inside the through-hole, a shaft 10, which will be described later, is disposed. In the same manner, at the upper portion of the spring unit, a disk-shaped tip spring seat 21 is provided. In the tip spring seat 21, a cylindrically-shaped projection for fitting the compression spring 8a is provided at the lower portion, and the tip end of both ends of the spring unit is connected to the tip spring seat 21 by being fitted on this projection. Further, the tip spring seat 21 is provided with a through-hole extending in the vertical direction. Inside the through-hole, a shaft 10, which will be described later, is disposed. The shaft 10 is a vertically extended member provided so as to pass through insides of the plurality of compression springs 8a and 8b, the shaft being connected to one end of the spring unit configured by connecting the compression springs and configured to support the junction spring seat 9 in an upwardly and downwardly movable manner. Further, the tip spring seat 21 is configured to guide the shaft 10. The tip spring seat 21 is configured to be connected to a spring closer to the support column inner pulley 14 among the springs constituting the spring mechanism and configured to guide the shaft 10.

In the hollow portion of the support column 2, a partition wall 22 for supporting the tip spring seat 21 is provided. The partition wall 22 is provided so as to divide the hollow portion of the support column into an upper part and a lower part, and also is provided with a through-hole extending in the vertical direction for passing through the shaft 10. The partition wall 22 is fixed to the inner wall of the support column 2 and prevents the tip spring seat 21 from moving upward in the support column 2. The partition wall 22 corresponds to the "unit fixing member" of the present invention. The partition wall 22 fixes the other end of the spring unit to the support column 2.

The shaft 10 is a rod-shaped structure extending in the vertical direction from the lower end of the spring unit as a starting point, passing through the inside of the coiled spring unit, and protruding from the upper end of the spring unit, and extends in the vertical direction. At the tip of the shaft 10 which is positioned at the lower end of the spring unit, a screw thread is cut and the nut is screwed into the screw thread. This nut is located on the lower side of the end spring seat 11 and is supported by the shaft 10. The nut prevents the falling of the end spring seat 11 positioned at the top of the nut. This nut prevents the decomposition of the spring unit.

The spring unit is extendable and contractible in the vertical direction. When the spring unit extends/contracts, following it, the shaft 10, the end spring seat 11 and the junction spring seat 9 constituting the spring unit move upward and downward in the vertical direction so as to follow the expansion/contraction. At this time, although the shaft 10, the end spring seat 11, and the junction spring seat 9 move in the same direction, the movement amount of the end spring seat 11 is larger than the movement amount of the junction spring seat 9. This is because the displacement amount of the spring increases as it goes to the end. Further, since the shaft 10 and the end spring seat 11 are fixed, even if the spring unit is extended or contracts, there is no change in the relative position. Further, when the spring unit extends and contracts, the tip spring seat 21 is restrained by the partition wall 22 and therefore does not move, but the relative position between the tip spring seat 21 and the shaft 10 changes.

In the through-hole of the junction spring seat 9, a bearing (not shown) is provided for the purpose of smoothly guiding the shaft 10.

At the end of the shaft 10 of both ends of the shaft 10 protruded from the upper end of the spring unit, an arm A supporting the above-described movable pulleys 13b is provided in a fixed state. In this figure, the arm A has a U-shape. At each of the tips of the arm A, a movable pulley 13b is provided. The arm A is fixed to the shaft 10. The movable pulleys 13b are supported by the arm A and disposed on both sides of the relay pulley 13a. The respective movable pulleys 13b are wound by the support column inner wire 12b.

The spring mechanism in this specification means a composite of the arm A, the compression springs 8a and 8b, the junction spring seat 9, the shaft 10, the end spring seat 11, the tip spring seat 21, and the movable pulley 13b.

The force that the spring mechanism of the present invention imparts to the support column inner wire 12b will be described. Since the spring unit is composed of the compression springs, it gives a force to keep the tip spring seat 21 and the end spring seat 11 away from each other. The tip spring seat 21 will not move inside the support column 2, so that the spring unit will give a descending force to the shaft 10. This force is transmitted to the movable pulley 13b located at the tip of the arm A. Thus, the support column inner wire 12b is given the force to push the wire down. That is, the force that extends the spring unit generates a force occurred at the movable pulleys 13b to push down the support column inner wire 12b.

Figure 7:
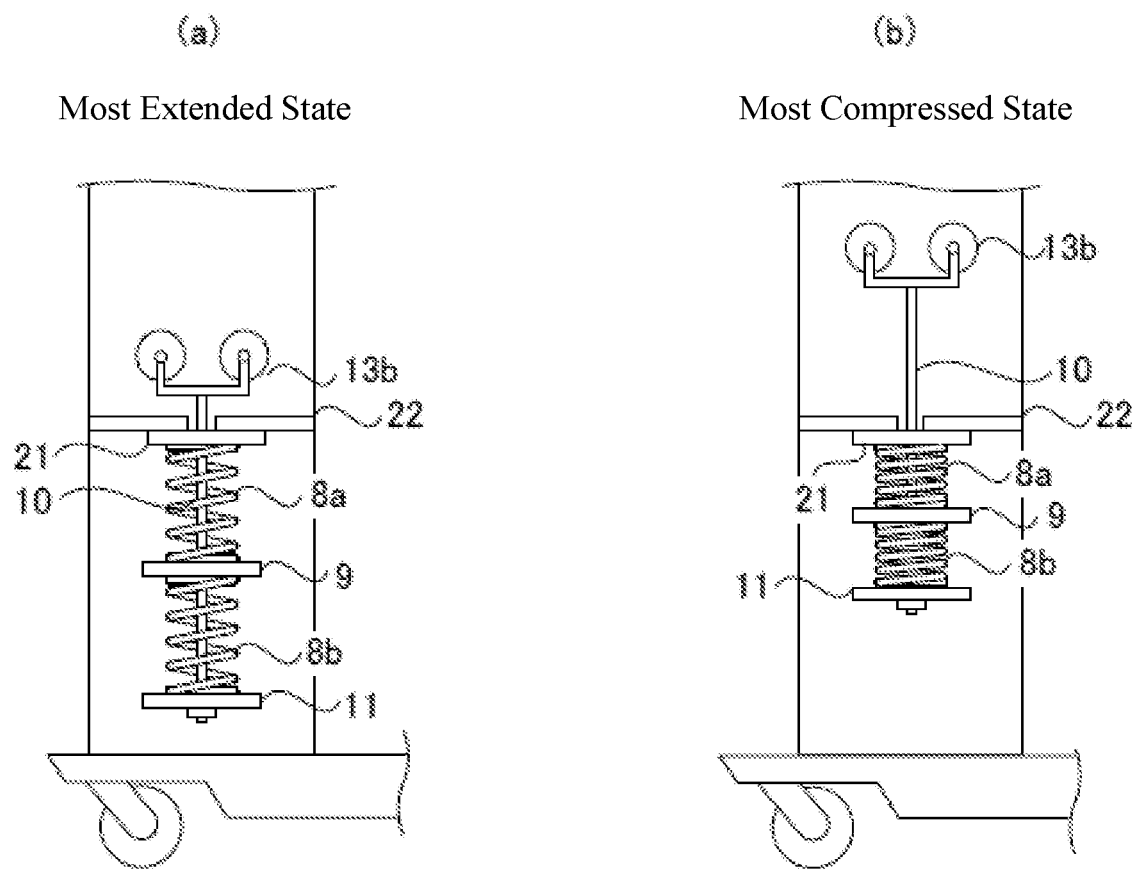
FIG. 7 is a cross-sectional view explaining an extension and compression of a spring unit according to Example 1.

FIG. 7 shows the state of extension and contraction of the spring unit. The left side of FIG. 7 shows the state in which the spring unit is most extended. At this time, the X-ray tube 6 is most moved upward, and does not move further upward from this position. Even in this case, the compression springs 8a and 8b constituting the spring unit still have the power to extend. Therefore, the force of moving the tip spring seat 21 and the end spring seat 11 away from each other is maintained although it is weak.

On the other hand, the left side of FIG. 7 shows the state in which the spring unit is most compressed. At this time, the X-ray tube 6 is most moved downward, and does not move further downward from this position. Even in this case, the compression springs 8a and 8b constituting the spring unit is most compressed. Therefore, the force for keeping the tip spring seat 21 and the end spring seat 11 away from each other becomes the strongest state.

As described above, since the strength of the force applied to the shaft 10 is changed by the expansion and compression of the spring unit, the strength of the force of pushing down the support column inner wire 12b also changes. However, the operator who operates the X-ray tube 6 does not feel this change. This is because the change in force of depressing the support column inner wire 12b downward is offset by the support column inner pulley 14 having the spiral.

Effects of Present Invention

Figure 8:
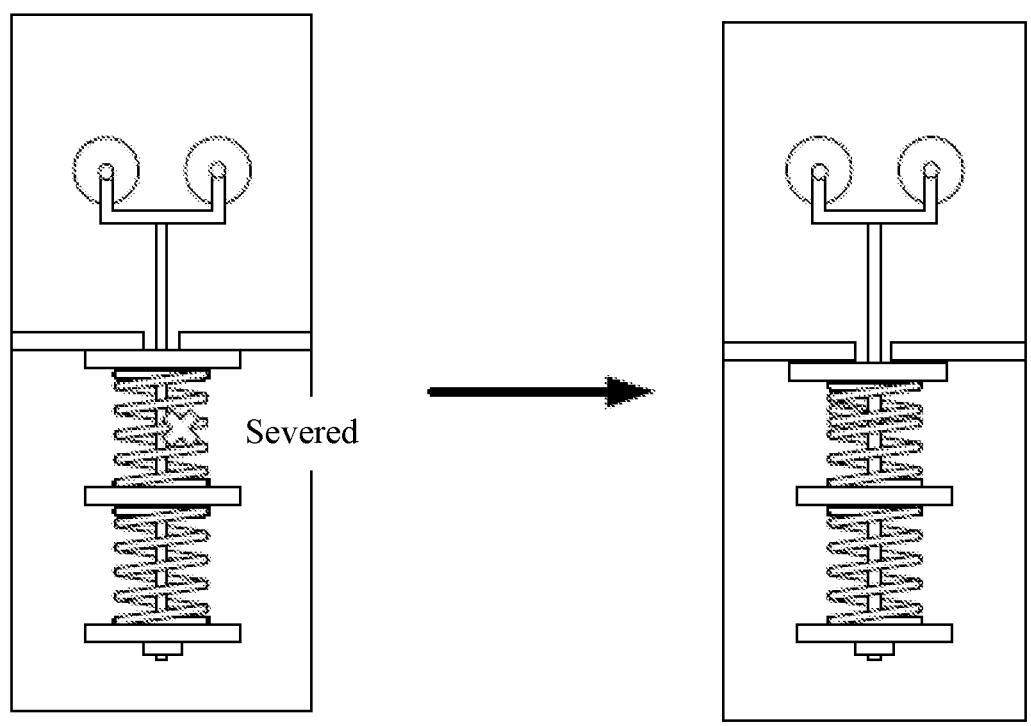
FIG. 8 is a cross-sectional view explaining effects of the configuration according to Example 1.

Next, the effects of the present invention will be described. FIG. 8 shows the case in which the compression spring 8a is severed due to the aged deterioration or the like. Even if the compression spring 8a is severed, the respective fragments try to stretch. Then, the fragments get caught each other and prevent the respective extensions. The difference between before and after the compression spring 8a is severed is that the compression spring 8a in a coil form has been shortened by one pitch. Therefore, when the spring is severed, the spring becomes shorter by one pitch, so that the X-ray tube 6 drops a distance corresponding to it, but the situation of falling indefinitely does not occur.

Figure 14:
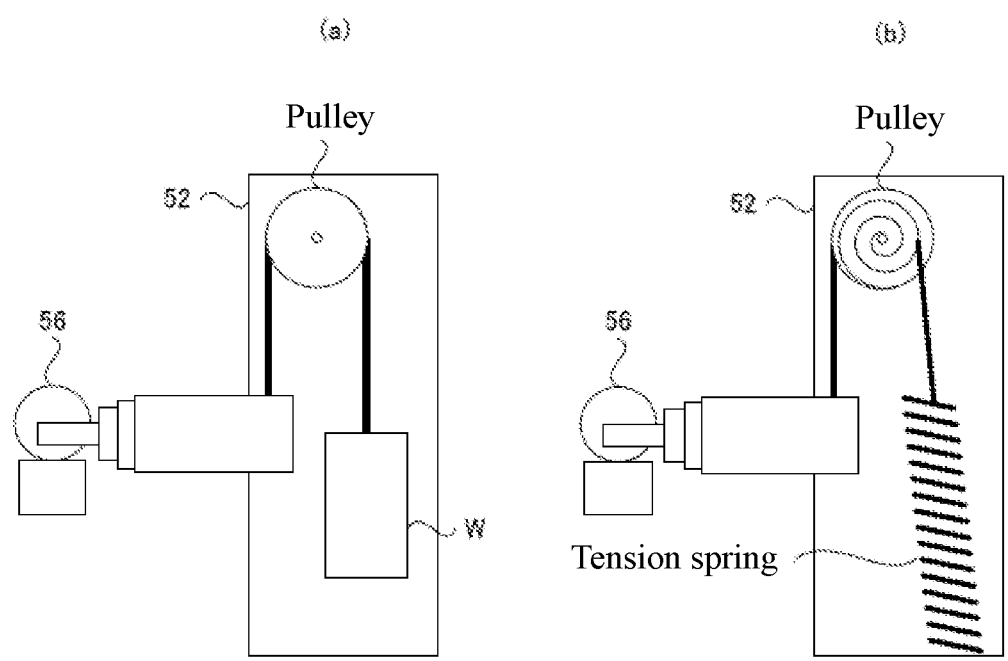
FIG. 14 is a schematic diagram explaining a configuration of the moving-type radiation device of the conventional configuration.
Figure 15:
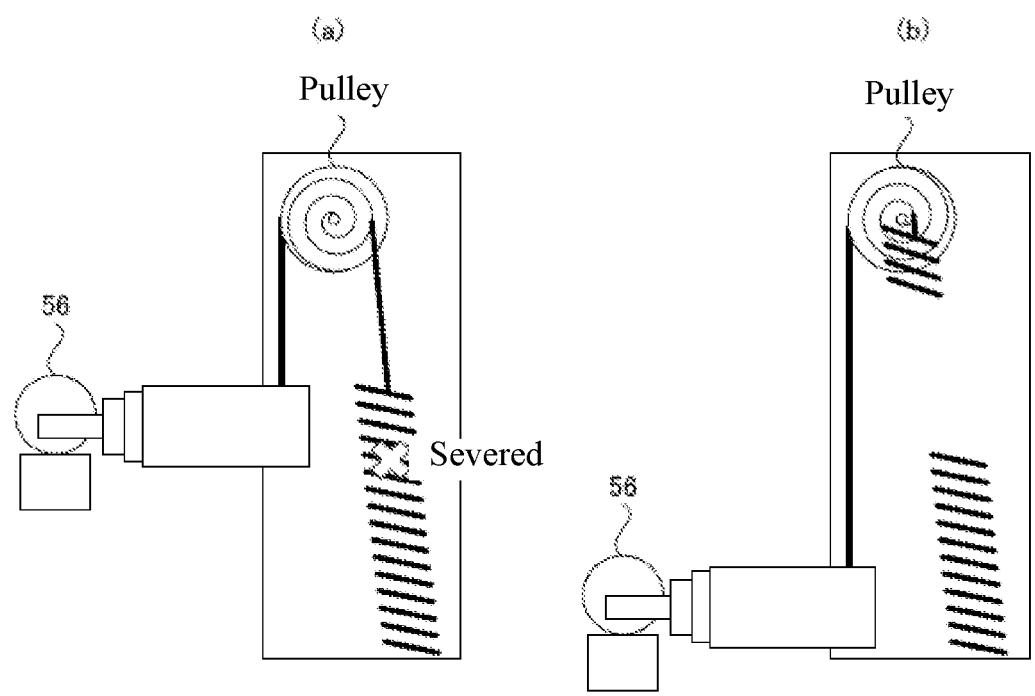
FIG. 15 is a schematic diagram explaining the problems of the moving-type radiation device of the conventional configuration.

In this way, when the compression spring is used instead of the counter weight described on the left side of FIG. 14, it helps to maintain the safety of the device, but there are difficult problems to solve. Unlike the tension spring, the compression spring is difficult to secure the stroke. The tension spring is suitable for a mechanism having a long stroke. If it is desired to lengthen the stroke, it is enough to lengthen the spring. However, a compression spring cannot earn a stroke with the same principle. A compression spring has its own problem of buckling.

A compression spring has a characteristic that it becomes easier to bend as it gets longer. A compression spring is used in such a way that a pressure is applied from both sides of the spring, but as the spring becomes longer, the middle of the spring is likely to escape in a direction orthogonal to the extension direction of the spring. As a result, the spring will bend and will not fulfill its original function.

So, what has been devised in the present invention is a junction spring seat 9. With this, even in cases where the compression springs are linked in series, the compression springs will not be buckled. That is, the junction spring seat 9 is configured to be guided by the shaft 10, and does not escape in the lateral direction orthogonal to the extension direction of the spring. The compression springs 8a and 8b are supported by the junction spring seat 9 and cannot escape in the lateral direction. On the other hand, the individual compression springs 8a and 8b are short enough that they will not be buckled. As a result, the spring will not bend and exert its original function.

The present invention is not limited to the aforementioned configuration, and may be modified as follows.

Figure 9:
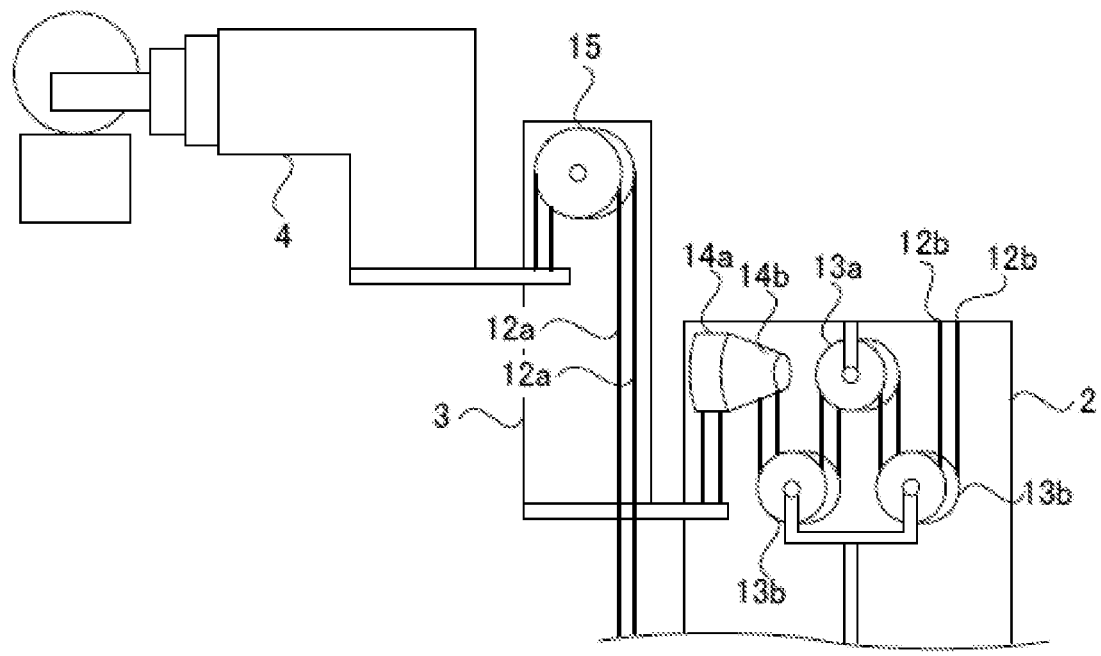
FIG. 9 is a cross-sectional view explaining one modified example of the present invention.

(1) According to the above-described Example, there are only one winding pulley wire 12a and only one support column inner wire 12b, but the configuration of the present invention is not limited thereto. As shown in FIG. 9, the winding pulley wire 12a and the support column inner wire 12b can be doubled. With such a configuration, even in cases where one of the winding pulley wire 12a and the support column inner wire 12b is severed, the remaining un-severed wire can support the X-ray tube 6, which prevents the dropping of the X-ray tube 6. Note that the winding pulley wire 12a and the support column inner wire 12b can be tripled or more.

Similarly, according to the above-described example, there was only one intermediate member wire 23, but the configuration of the present invention is not limited thereto. As shown in FIG. 9, the intermediate member wire 23 may be multiplexed. With such a configuration, even in cases where one of the intermediate member wires 23 is severed, the remaining non-severed wire can support the X-ray tube 6, which prevents the dropping of the X-ray tube 6. Further, the intermediate member wire 33 may be tripled or more.

In FIG. 9, the winding pulley wire 12a, the support column inner wire 12b, and the intermediate member wire 23 are multiplexed, but it is also possible to select one of them and configure it in multiple.

Figure 10:
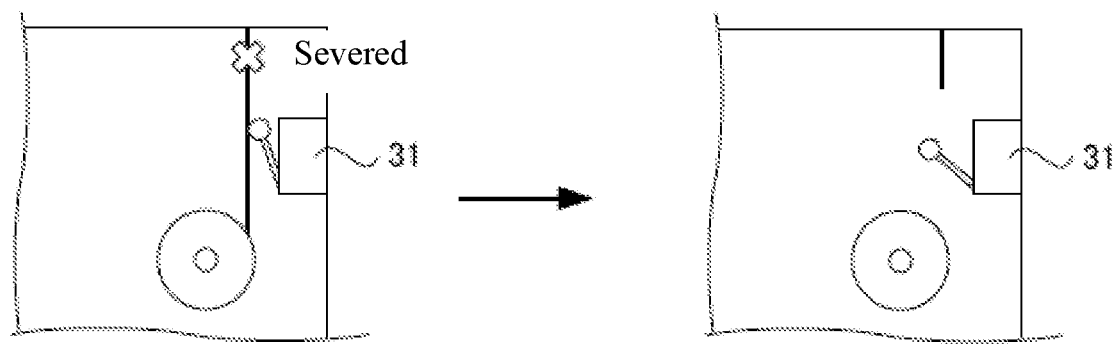
FIG. 10 is a cross-sectional view explaining one modified example of the present invention.

(2) According to the above-described Example, there is no description on a configuration for sensing the severing of the support column inner wire 12b, but a sensor 31 for detecting the tension of the wire may be provided as shown in FIG. 10. The sensor 31 is provided with such an arm which is moved downward when a downward force is applied and is moved upward when the force is released. The sensor 31 is an electronic component that turns ON when the arm is pushed down, and turns OFF when the arm is raised. The sensor 31 is mounted in the support column 2 so that its arm is pressed against the support column inner wire 12b and is in the ON state when the arm is pushed down by the support column inner wire 12b. A spherical reinforcing member is provided at the tip of the arm of the sensor 31, and wearing of the arm of the sensor 31 is prevented by the support column inner wire 12b.

When the support column inner wire 12b is severed, the force pushing downward the arm disappears, so that the arm is pushed upward by itself and the sensor 31 is turns OFF. At this point, the moving-type X-ray device executes an alarm to notify the operator of the severing of the wire based on the output of the sensor 31. Such a modified Example is suitable for the configuration as shown in FIG. 9 in which wires are multiplexed. That is, with the configuration as shown in FIG. 9, even if one wire is broken, a normal operation can be performed by another wire. However, if it is left unattended, it may happen that the severed wire tangles and damages the structure inside the support column 2. Therefore, it is better to transmit the severing of the wire to the operator as soon as possible. In cases where the wires are multiplexed as shown in FIG. 9, the sensor 31 is provided for each of the two support column inner wires 12b.

The sensor 31 in this modified example is an electronic component that turns ON when the arm is pushed down and turns OFF when the arm is pushed up. Instead of this, it is possible to construct this modified example by using a sensor 31 that turns OFF when the arm is pushed down and ON when the arm is pushed up.

(3) In Example 1, it is configured such that the two compression springs 8a and 8b are linked to form the spring unit, but three or more compression springs may be linked to form a spring unit.

Figure 11:
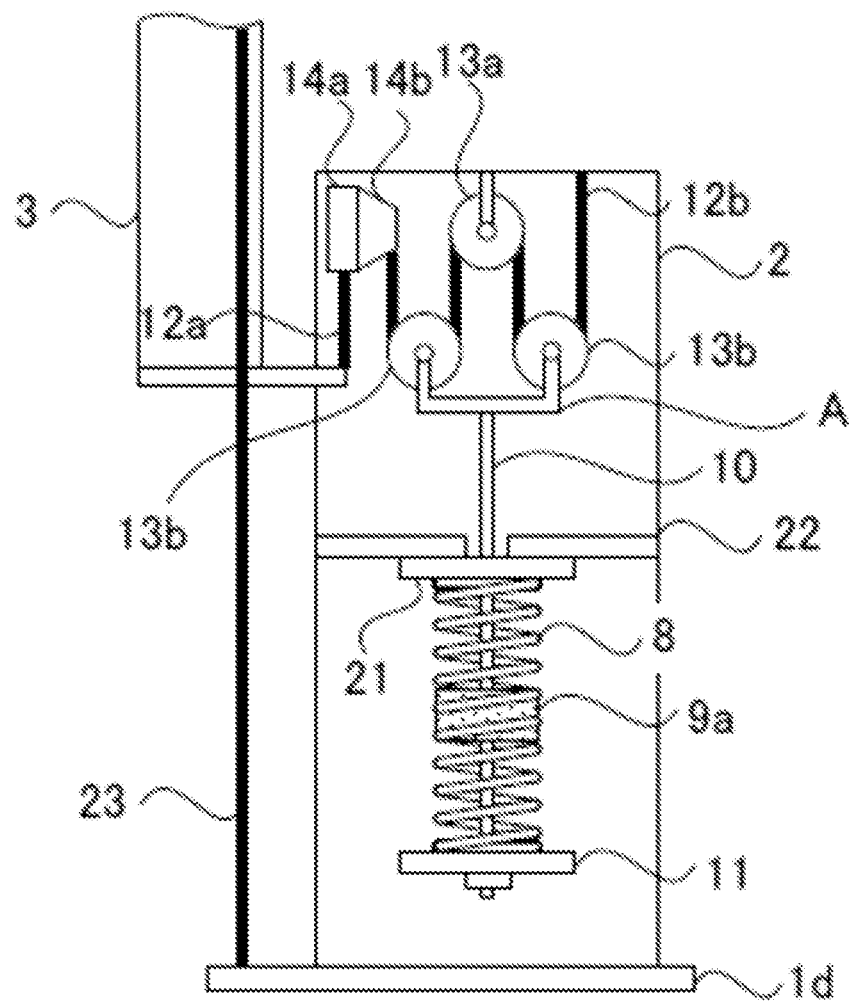
FIG. 11 is a cross-sectional view explaining one modified example of the present invention.

(4) In Example 1, it is configured such that the two compression springs 8a and 8b are linked to form the spring unit, but a single compression springs can realize the present invention. FIG. 11 shows a device according to the modified example. This device is characterized by the spring unit. That is, the spring unit is composed of a single long compression spring. Normally, if the compression spring is so long, it will be buckled soon, but in this modified example, it is devised to suppress this problem.

Figure 12:
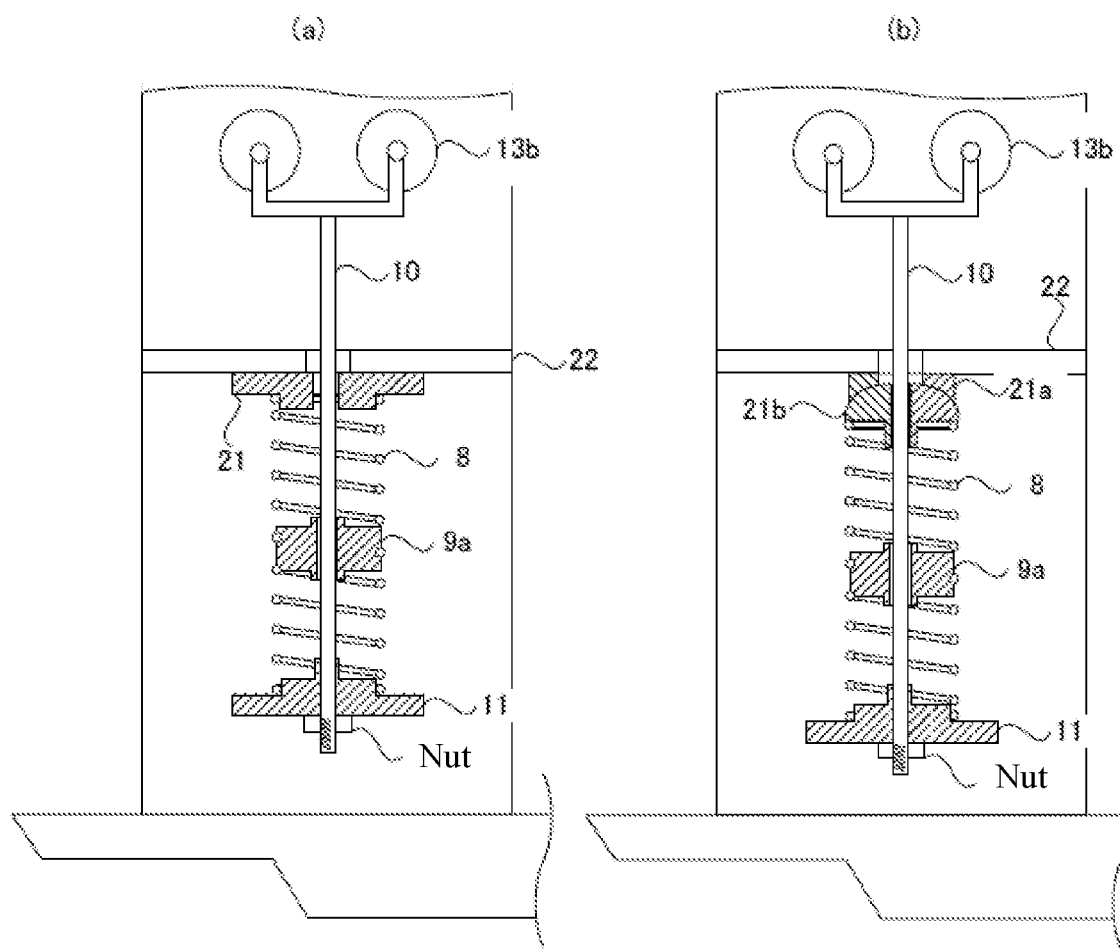
FIG. 12 is a cross-sectional view explaining one modified example of the present invention.
Figure 13:
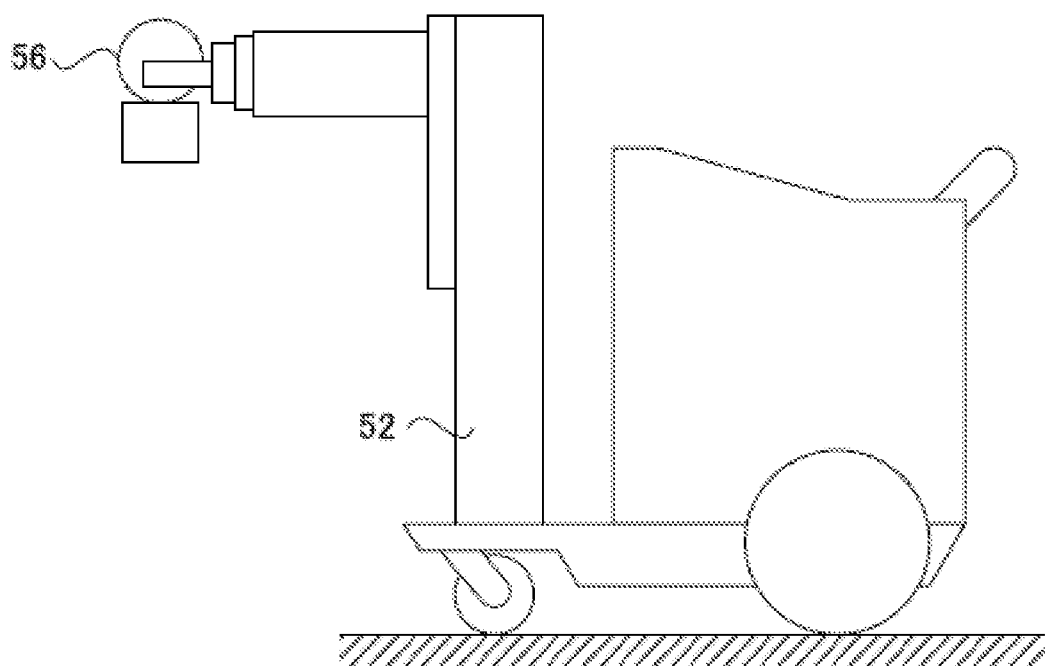
FIG. 13 is a schematic diagram explaining a configuration of a moving-type radiation device of a conventional configuration.

An intermediate connector 9a is fixed in the middle of the compression spring of this modified example. The structure of the intermediate connector 9a will be described. FIG. 12(a) is a conceptual diagram for more easily explaining the structure of the spring mechanism. In FIG. 12(a), the cross-section of the compression spring 8a and its peripheral components are shown so that the inside of the compression spring 8a can be easily understood. The intermediate connector 9a has a cylindrical shape, and a side surface is engraved with a helical groove into which a compression spring fits. Further, the intermediate connector 9a is provided with a through-hole extending in the vertical direction. Inside the through-hole, a shaft 10 is disposed. In the through-hole of the intermediate connector 9a, a bearing is provided for the purpose of smoothly guiding the shaft 10. The intermediate connector 9a is fixed in the middle of the compression spring 8. The shaft 10 is provided so as to pass through an inside of the compression spring 8. The shaft is connected to one end of the compression spring 8. The shaft is a member configured to support the intermediate connector 9a in an upwardly and downwardly movable manner and extend in the vertical direction.

The present invention has a configuration which can exert the same effects described above with one compression spring. The intermediate connector is configured to be guided by the shaft, and does not escape in the lateral direction orthogonal to the extending direction of the spring. Each part of the compression spring divided by the intermediate connector is sufficiently short and it will not be buckled.

(5) Although Example 1 has two movable pulleys, the present invention is not limited to this configuration. One movable pulley may be used, or three or more may be used.

(6) In Example 1, two wires fixed to the respective spiral pulley 14a and winding pulley 14b are provided, but the present invention is not limited to this configuration. On the inner surface corresponding to the ceiling of the internal space of the support column, there is provided a fixing tool for fixing the tip of a wire. Similarly, the intermediate member 3 is also provided with a fixing tool. It is also possible to configure such that a single support column inner wire is provided between the fixing tool inside the support column and the fixing tool of the intermediate member 3.

In this case, the support column inner wire is held in the form wound around the support column inner pulley 14. Therefore, the support column inner wire is held so as to unwind to the lower side of the support column inner pulley 14 after winding from the lower side of the support column inner pulley 14. The support column inner pulley 14 is constituted by two parts fixed each other, i.e., a winding pulley 14b and a spiral pulley 14a. The central axis of the part of the winding pulley 14b is the rotation axis of the support column inner pulley 14. In the portion of the winding pulley 14b, a coiled groove is formed and the groove continues to the tapered portion. The groove of the spiral pulley 14a is provided with a spiral groove such that the curvature gradually increases as it goes away from the portion of the winding pulley 14b and when viewed from the rotation axis direction of the support column inner pulley 14, the spiral pulley 14a becomes a spiral shape. The support column inner pulley 14 is served as a fixed pulley for the support column 2. The support column inner pulley 14 supports the support column inner wire. The support column inner wire is fixed at the border between the spiral of the support column inner pulley 14 and the cylindrical part.

(7) According to Example 1, the tip spring seat 21 is composed of a single member, but the present invention is not limited to this configuration. As shown in FIG. 12(b), the tip spring seat 21 may be composed of a receiving member 21a connected to the partition wall 22 and a covering member 21b covering the shaft 10 and connecting to the receiving member 21a on the lower side. The receiving member 21a is a ring-shaped member, and has a through-hole that allows the shaft 10 to pass through in the center. The covering member 21b is a mushroom-shaped member, and has a through-hole at the center to allow the shaft 10 to penetrate therethrough. The covering member 21b guides the shaft 10 moving in the vertical direction and prevents the shaft 10 from tilting. By configuring the tip spring seat 21 as described in this modified example, the spring buckling resistance of the spring 8a can be further improved. Note that the covering member 21b is engaged with the spring 8a.

Further, a self-aligning mechanism may be provided in the tip spring seat 21 itself. With this configuration, even if the shaft 10 is inclined, a large force from the shaft 10 is not applied to the covering member 21b and therefore no friction occurs between the covering member 21b and the shaft 10, so that the movements of the shaft 10 become smooth.

INDUSTRIAL APPLICABILITY

As described above, the present invention is suitably applicable in the medial field.

DESCRIPTION OF REFERENCE SYMBOLS

1 chassis
2 support column
3 intermediate member
6 X-ray source (radiation source)
8a, 8b compression spring
9 junction spring seat
12 support column inner wire
13a relay pulley
13b movable pulley
14 support column inner pulley
15 intermediate member pulley
21(21a, 21b) tip spring seat
22 intermediate member wire

The invention claimed is:

1. A moving-type radiation device comprising:
a radiation source configured to irradiate radiation;
a support column configured to support the radiation source in an upwardly and downwardly movable manner and extending in a vertical direction;
an intermediate member provided at a position between the radiation source and the support column so as to be upwardly and downwardly movable in accordance with upward and downward movements of the radiation source;
a support column inner wire having one end connected to the intermediate member and the other end connected to an inside of the support column;
a support column inner pulley configured to support the support column inner wire and serve as a fixed pulley for the support column provided in the support column;
a movable pulley provided on the other end side of the support column inner wire when viewed from the support column inner pulley and configured to be wrapped to the support column inner wire and serve as a fixed pulley for the support column provided in the support column; and
a spring mechanism configured to give a tensile force to the support column inner wire and provided in the support column,
wherein the spring mechanism includes:
(A) a compression spring having an upper end and a lower end, the upper end being fixed inside the support,
(B) a shaft connected to the movable pulley at one end, penetrating the compression spring through an upper end of the compression spring, and fixed to a lower end of the compression spring.

2. The moving-type radiation device as recited in claim 1, further comprising:
a tip spring seat connected to the compression spring constituting the spring mechanism and configured to guide the shaft.

3. The moving-type radiation device as recited in claim 2, wherein the tip spring seat is provided with a self-aligning mechanism.

4. The moving-type radiation device as recited in claim 1, further comprising:
an intermediate member wire having one end connected to the radiation source and the other end connected to the support column or a base on which the support column is installed; and
an intermediate member pulley configured to support the intermediate member wire and serve as a fixed pulley for the intermediate member.

5. The moving-type radiation device as recited in claim 4, wherein the intermediate member wire is multiplexed.

6. The moving-type radiation device as recited in claim 1, wherein the support column inner wire is multiplexed.

7. The moving-type radiation device as recited in claim 1, further comprising:
a sensor configured to sense severing of the support column inner wire.

8. The moving-type radiation device as recited in claim 1, further comprising:
a tip spring seat connected to a spring closer to the support column inner pulley among the springs constituting the spring mechanism and configured to guide the shaft.

9. The moving-type radiation device as recited in claim 1, further comprising:
an intermediate member wire having one end connected to the radiation source and the other end connected to the support column or a base on which the support column is installed; and
an intermediate member pulley configured to support the intermediate member wire and serve as a fixed pulley for the intermediate member.

10. The moving-type radiation device as recited in claim 1, wherein the intermediate member wire is multiplexed.

11. The moving-type radiation device as recited in claim 1, wherein the support column inner wire is multiplexed.

12. The moving-type radiation device as recited in claim 1, further comprising:

a sensor configured to sense severing of the support column inner wire.

\* \* \* \* \*